(12) United States Patent
Davis et al.

(10) Patent No.: US 6,740,500 B1
(45) Date of Patent: May 25, 2004

(54) METHOD OF SCREENING FOR NON-STEROIDAL NEUROPSYCHIATRIC AGENTS

(76) Inventors: John M. Davis, 442 Webster Ave., Chicago, IL (US) 60614; Doncho P. Uzunov, 910 S. Michigan Ave., Apt. #816, Chicago, IL (US) 60605

( * ) Notice: Subject to any disclaimer, the term of this patent is extended or adjusted under 35 U.S.C. 154(b) by 0 days.

(21) Appl. No.: 09/534,831

(22) Filed: Mar. 23, 2000

(51) Int. Cl.$^7$ .................. G01N 33/567; C12Q 1/26; C12P 21/06; C07H 21/04; C07K 1/00

(52) U.S. Cl. .............. 435/25; 435/6; 435/7.1; 435/7.21; 435/69.1; 436/501; 530/350; 536/23.1; 514/2

(58) Field of Search ................ 435/25, 6, 7.1, 435/7.21, 69.1; 436/501; 530/350; 536/23.1; 514/2

(56) References Cited

PUBLICATIONS

Uzunov et al., PNAS 93(12599–12604) 1996.*
Penning et al., Purification and properties of 3 alpha–hydroxysteroid dehydrogenase from rat brain cytosol. Inhibition by nonsteroidal anti–inflammatory drugs and progestins. J. Biol. Chem., Dec. 1985, 5;260(28):15266–72.*
Griffin and Mellon, Selective serotonin reuptake inhibitors directly alter activity of neurosteroidogenic enzymes., Proc. Natl. Acad. Sci., Nov. 1999, vol. 96, Issue 23, 13512–17.*
Baker, E.R., Best, R.G., Manfredi R.L., Demers, L.M., Wolf, G.C. (1995): Efficacy of Progesterone Vaginal Suppositories in Alleviation of Nervous Symptoms in Patients with Premenstrual Syndrome. *J. Assisted Reproduction and Genetics* 12:205–209.
Baulieu, E.E., Robel, P. (1990): Neurosteroids: A New Brain Function. J. Steroid Biochem. Mol. Biol. 37:395–403.
Blier, P., deMontigny, C. (1994): Current Advances and Trends in the Treatment of Depression. *Trends Pharmacol. Sci.* 15:220–226.
Britton, K., Koob, G. (1998): Premenstrual Steroids? *Nature* 392:869–870.
Cheney, D.L., Uzunov, D., Costa, E., Guidotti, A. (1995a): Gas Chromatographic Mass Fragmentographic Quantitation of 3α–Hydroxy–5α–pregnant–20–one (Allopregnanolone) and Its Precursors in Blood and Brain of Adrenalectomized and Castrated Rats. *J. Neurosei.* 15:4641–4650.
Costs, E., Cheney, D.L., Grayson, D.R., Korneyev, A., Longone P. Sani, L., Romeo, E. Zivkovic, E., Guidotti, A. (1994): Pharmacology of Neurosteroid Biosynthesis: Role of Mitochondrial DBI Receptor (MDR) complex. *Ann. NY Acada. Sci.* 746:223–242.

Costa, E., Auta J. Caruncho, H., Guidotti, A., Impagnatiello, F., Pesold, C., Thompson, D.M. (1995): A Search for a New Anticonvulsant and Anxiolytic Benzodiazepine Devoid of Side Effects and Tolerance Liability. In: Bigio, G., Sanna, E., Costa, E., editors. GABA, *Receptors and Anxiety: from Neurobiology to Treatment*. New York: Raven Press, pp. 75–92.

Eriksson, E., Hedberg, M.A., Andersch, B. Sundblad, C. (1995): The Serotonin Reuptake Inhibitor Paroxetine Is Superior to the Noradrenaline Reuptake Inhibitor Maprotiline in the Treatment of Premenstrual Syndrome. *Neuropsychopharmacol.* 12:167–176.

Favale, E. Rubino, V., Mainardi, P. Albano, C. (1995): Anticonvulsant Effect of Fluoxetine in Humans. *Neurology* 45:1926–1927.

Fuller, R.W., Wong, D.T., Robertson, D.W. (1991): Fluoxetine, a Selective Inhibitor of Serotonin Uptake. *Med. Res. Rev.* 11:17–34.

Gee, K.W., McCauley, D.L., Lan, N.C. (1995): A Putative Receptor for Neurosteroids on the $GABA_A$ Receptor Complex: The Pharmacological Properties and Therapeutic Potential of Epalons. *Crit. Rev. Neurobiol.* 9:107–227.

Guidotti, A., Uzunov, D., Auta, J., Costa, E. (1996): Application of Gas Chromatography Mass Fragmentography with Negative Ion Chemical Ionization Technology to Measure Neurosteroids and Their Biosynthesis Rate in the Rat Brain In: Genazzani, A.R., Petraglia, F., Purdy, R.H., editors, *The Brain: Source and Target for Sex Steroid Hormones*. New York: Parthenon, pp. 25–41.

Karavolas, H.J., Hodges, D.R., (1991): Metabolism of Progesteronie and Related Steroids by Neuronal and Neuroendocrine Structures. In: Costa, E., Paul, S.M., editors, *Neurosteroids and Brain Functions*. New York: Theine, pp. 135–145.

(List continued on next page.)

*Primary Examiner*—Yvonne Eyler
*Assistant Examiner*—Michael Brannock
(74) *Attorney, Agent, or Firm*—Seyfarth Shaw LLP

(57) ABSTRACT

A method of screening for non-steroidal neuropsychiatric agents includes determining the ability of a candidate non-steroidal agent to selectively regulate or alter the central nervous system content and/or bioavailability of an endogenous neuroactive steroid. In particular, the method includes determining the ability of the agent to selectively regulate a rate-limiting step in the bio-control of the bioavailable amount of an endogenous neuroactive steroid, wherein the rate-limiting step may be either a step in biosynthesis of an endogenous neuroactive steroid, such as allopregnanolone, or a step in the biodegradation of such an endogenous neuroactive steroid. Alternatively, the method may include determining the ability of a candidate agent in selectively regulating the rate of reuptake of an endogenous neuroactive steroid by neurons or glial cells.

7 Claims, 1 Drawing Sheet

OTHER PUBLICATIONS

Matsumoto, K., Uzunova, V., Pinna, G. Taki, K. Uzunov, D.P., Wantanbe, H., Mienville, J.M., Guidotti, A., Costa, E. (1999): Permissive Role of Brain Allopregnanolone Content in the Regulation of Pentobarbital–Induced Righting Reflex Loss, *Neuropharmacol.* 38(7):955–964.

McEwen, B.S. (1991): Nongenomic and Genomic Effects of Steroids on Neuronal Activity. *Trend Pharmacol. Sci.* 12:141–147.

Paul, S.M., Purdy, R.H. (1992): Neuroactive Steroids. FASEB J. 6:2311–2322.

Rapkin, A.J., Morgan, M., Goldman, L., Brann, D. Simone, D., Mahesh, V. (1997): Progesterone Metabolite Allopregnanoline in Women with Premenstrual Syndrome. *Obstetrics & Gynecol.* 90 (5): 709–714.

Romeo, E. Auta, J. Kozikowski, P., Ma, D., Papadopoulos, V., Puia, G. Costa, E., Guidotti, A. (1992): 2 Aryl–3–Indoleacetamides (FGIN–1): A New Class of Potent and Specific Ligands for the Mitochondrial DBI Receptor (MDR). *J. Pharmacol. Exp. Ther.* 262:971–976.

Romeo, E., Strohle, A. Spalleta, G., diMichele, F., Hermann, B., Holsboer, F. Pasini, A., Rupprecht, R. (1998): Effects of Antidepressant Treatment on Neuroactive Steroids in Major Depression. *Am. J. Psychiatry* 155: 910–913.

Steiner, M., Steinberg, S. Stewart, D., Carter. D., Berger, C., Reid, R., Grover, D., Steiner, D. (1995): Fluoxetine in the Treatment of Premenstrual Dysphoria. *N. Engl. J. Med.* 332:1529–1534.

Su, T.P., Schmidt, P.J., Danaceau, M.A., Tobin, M.B., Rosenstein, D.L., Murphy, D.L., Rubinow, D.R. (1997): Fluoxetine in the Treatment of Premenstrual Dysphoria. *Neuropsychopharmacol.* 16(5):346–356.

Uzunov, D.P., Cooper, T.B., Costa, E., Guidotti, A. (1996): Fluoxetine–Elicited Changes in Brain Neurosteroid Content Measured by Negative Ion Mass Fragmentography. *Proc. Natl. Acad. Sci. USA* 93:12599–12604.

Uzunova, V., Sheline, V., Davis, J.M., Rasmusson, A., Uzunov, D.P., Costa, E., Guidotti, A. (1998): Increase in the Cerebrospinal Fluid Content of Neurosteroids in Patients with Unipolar Major Depression Who Are Receiving Fluoxetine or Fluvoxamine. *Proc. Natl. Acad. Sci. USA* 95:3239–3244.

Yonkers, K.A., Halbreich, V., Freeman, E., Brown, C. Pearlstein, T. (1996): Sertraline in the Treatement of Premenstrual Dysphoric Disorder. *Psychopharmacol, Bull.* 32:41–46.

* cited by examiner

METHOD OF SCREENING FOR NON-STEROIDAL NEUROPSYCHIATRIC AGENTS

BACKGROUND OF THE INVENTION

The present invention relates to methods of identifying or screening for drugs or agents useful in treatment of psychiatric or neurological disorders, and relates in particular to screening for non-steroidal drugs or agents.

The present invention is based, in part, on experimental work, some of which is reported in the following articles, the disclosures of which are incorporated herein by reference:

(a) Cheney, D. L., Uzunov, D., Costa, E., Guidotti, A. (1995a); Gas chromatographic mass fragmentographic quantitation of 3α-hydroxy-5α-pregnan-20-one (allopregnanolone) and its precursors in blood and brain of adrenalectomized and castrated rats. *J. Neurosei*, 15:4641–4650.

(b) Cheney, D. L., Uzunov, D., Guidotti, A. (1995b): Pregnanolone sulfate antagonizes dizocilpine amnesia: Role for allopregnanolone. *NeuroReport* 6:1697–1700.

(c) Guidotti, A., Uzunov, D., Auta, J., Costa, E. (1996): Application of gas chromatography mass fragmentography with negative ion chemical ionization technology to measure neurosteroids and their biosynthesis rate in the rat brain In: Genazzani, A. R., Petraglia, F., Purdy, R. H., editors. *The Brain: Source and Target for Sex Steroid Hormones*. New York:Parthenon, pp 24–41.

(d) Uzunov, D. P., Cooper, T. B., Costa, E., Guidotti, A. (1996): Fluoxetine-elicited changes in brain neurosteroid content measured by negative ion mass fragmentography. *Proc. Natl. Acad. Sci. USA* 93:12599–12604.

(e) Uzunova, V., Sheline, Y., Davis, J. M., Rasmusson, A., Uzunov, D. P., Costa, E., Guidotti, A. (1998): Increase in cerebrospinal fluid content of neurosteroids in patients with unipolar major depression who are receiving fluoxetine or fluvoxamine. *Proc. Natl. Acad. Sci. USA* 95: 3239–3244.

(f) Matsumoto, K., Uzunova, V., Pinna, G., Taki, K., Uzunov, D. P., Watanabe, H., Mienville, J. M., Guidotti, A., Costa, E. (1999): Permissive role of brain allopregnanolone content in the regulation of pentobarbital-induced righting reflex loss. *Neuropharmacol*, 38(7):955–964.

It is becoming increasingly clear that naturally-occurring steroidal modulators of neuronal function do exist in the brain acting as very potent endogenous regulators of the function of the brain's most abundant inhibitory (γ-aminobutyric acid) or excitatory (glutamatergic) neurotransmitter systems. The central nervous system (CNS) has the capacity to synthesize such steroids de novo from cholesterol independently of peripheral hormonal sources. These steroids are referred to herein as "neurosteroids." Neurosteroids that are pharmacologically potent modulators of neuronal activity are defined herein as neuroactive steroids. The pharmacological response induced by some neurosteroids is similar to that of the benzodiazepines (Valium-like drugs), and in non-technical language are likely to be the brain's own naturally occurring Valium-like compounds. Specifically, the neurosteroid 5α-pregnan-3α-ol-20-one (allopregnanolone, ALLO) at low nanomolar concentrations positively modulates γ-aminobutyric acid type A ($GABA_A$) receptor function, rapidly affecting brain excitability.

An example of biosynthesis of neurosteroids from cholesterol is illustrated in FIG. 1, which shows the major metabolic pathway for neurosteroid biosynthesis in the CNS. Pregnenolone (PREG) is formed from cholesterol by the cytochrome $P_{450}$ side chain cleavage ($P_{450SCC}$) enzyme. PREG is transformed into progesterone (PROG) by 3β-hydroxysteroid dehydrogenase isomerase (3β-HSD) and PROG is transformed into 5α-dihydroprogesterone (5α-DHP) by 5α-reductase. Finally, ALLO can be synthesized from 5α-dihydroprogesterone. (5α-DHP) by the action of the 3α-hydroxysteroid oxidoreductase (3α-HSOR) enzyme. This enzyme has two reversible functions—oxidative and reductive. The reduction of 5α-DHP to ALLO is dependent upon the availability of the cofactors NADPH or NADH, whereas the opposite step, which catalyzes the oxidation of ALLO to 5α-DHP is NAD/NADP dependent. Currently, the major pathway of ALLO metabolism and deactivation in the brain is thought to be the degradation of ALLO to 5α-DHP by the oxidative action of the 3α-HSOR. We have demonstrated that ALLO is unevenly distributed in brains of adrenalectomized and castrated (ADX/CX) rats, suggesting the existence of local regulatory mechanisms for its production and metabolism.

Referring to FIG. 2, in addition to the conversion to 5α-DHP by the 3α-HSOR, an alternative route for the deactivation of allopregnanolone is through the metabolism to 20α-hydroxyallopregnanolone (5α-pregnan-3α,20α-diol) (20α-hydroxy ALLO) by the action of the 20α-hydroxysteroid dehydrogenase (20α-HSD). The 20α-HSD also metabolizes progesterone to 20α-hydroxyprogesterone (4-pregnen-20α-hydroxy-3-one)(20α-hydroxy PROG), thus decreasing the endogenous pool of progesterone available to be metabolized to 5α-DHP and ultimately to allopregnanolone. Since both actions of the 20α-HSD would result in a significant decrease in the CNS levels of allopregnanolone, non-steroidal compounds that selectively inhibit the 20α-HSD would prevent the 20α-HSD-mediated depletion of the neuroactive steroid allopregnanolone in the brain.

Measurements of allopregnanolone in brain microdialysates obtained from freely moving rats have revealed that allopregnanolone is present in the extracellular compartment. These findings strongly suggest that allopregnanolone is released by glial cells and neurons and it can accumulate in the synaptic cleft in concentrations sufficient to activate the $GABA_A$ receptor. It remains to be understood whether an active reuptake mechanism involved in maintaining a physiological synaptic concentration of allopregnanolone exists. If such a mechanism does exist, then potential inhibitors of the reuptake of allopregnanolone would increase its accumulation in the vicinity of its target receptor.

Several lines of evidence indicate that a potentiation of serotonergic neurotransmission underlies the therapeutic response to various types of antidepressants. Fluoxetine and other selective serotonin reuptake inhibitors (SSRIs) have a spectrum of clinical efficacy that is different, greater, and quite often superior to that of other antidepressants. Hence, it is becoming increasingly clear that the ability of SSRIs to enhance serotonin activity is not the only mechanism responsible for the large spectrum of favorable clinical actions of the SSRIs.

Furthermore, the etiologies of premenstrual dysphoric disorder (PMDD) and premenstrual syndrome (PMS) are of considerable relevance to neurosteroids as their symptoms (anxiety, mood fluctuations, susceptibility to seizures, etc.) are associated with a precipitous decline in circulating levels of progesterone and its $GABA_A$ receptor active metabolite ALLO. In a recent study, it has been concluded that subjects with PMS manifest significantly lower levels of serum ALLO in the luteal phase when compared to controls. Interestingly, fluoxetine has been shown to be effective in the treatment of premenstrual dysphoria, displaying a much faster therapeutic response than the usual lag of three to six weeks required for SSRIs to become effective in alleviating symptoms of depression, suggestive that an enhancement of serotonergic neurotransmission is not the only mechanism underlying, the therapeutic action of fluoxetine in premenstrual dysphoria.

However, substantial difficulties prevent a direct therapeutic intervention with neurosteroids. For example, the results of the systemic administration of the $3\alpha,5\alpha$-reduced derivatives of PROG, acting as positive allosteric modulators of GABA action at $GABA_A$ receptors, indicate that the doses required to elicit a clear anxiolytic, antidysphoric, and antiepileptic activity may also produce profound sedation, motor impairment, or ataxia. Furthermore, the endogenous neurosteroids have a very short metabolic half-life and thus a limited bioavailability. All these properties compromise the development of these naturally occurring compounds as therapeutic agents.

In view of the foregoing, several drug companies are producing synthetic analogs of neurosteroids in an attempt to develop new drugs for the treatment of neuropsychiatric disorders. For example, CoCensys, Inc. has created a variety of synthetic analogs of endogenous neuroactive steroids, called epalons, that are being clinically evaluated for anesthesia and various neurological and psychiatric disorders. These compounds, however, although possessing less metabolic liability than endogenous neurosteroids, are still highly lipophilic, giving rise to serious formulation problems and consequently to decreased CNS bioavailability, ultimately having compromised the development of these compounds as neuropsychiatric therapeutic agents.

SUMMARY OF THE INVENTION

Our approach to utilizing the therapeutic potential of neuroactive steroids is conceptually different. Judging from our accumulated experimental data we postulate that neurosteroids serve a physiological role as endogenous modulators of brain function. Moreover, we have clearly demonstrated the existence of a link between a deficiency in endogenous neurosteroid bioavailability and symptoms of depression. The screening technology that we have invented is unique in that it will aid the discovery and development of non-steroidal neuropsychiatric drugs that would regulate the endogenous levels of neuroactive steroids, as opposed to the prior approach of an exogenous administration of neurosteroids or synthetic neurosteroid-like compounds. Our screening technology is designed to identify compounds which would (a) selectively affect some rate-limiting steps of the biosynthesis of the endogenous neuroactive steroids in the brain, such as the conversion of $5\alpha$-DHP to ALLO and/or vice versa, the degradation of ALLO to $5\alpha$-DHP by the $3\alpha$-HSORs (see FIG. 1), or (b) would inhibit the reuptake of the endogenous neuroactive steroids by neurons or glial cells. These compounds are collectively termed Selective Neurosteroid Regulating Agents (SNRAs).

It is a general object of the invention to provide an improved approach to identifying neuropsychiatric drugs which avoids disadvantages of prior techniques and affords other advantages.

An important feature of the invention is the provision of a method of screening for non-steroidal neuropsychiatric agents based upon the ability of the agent to affect the bioavailability of endogenous neuroactive steroids.

In connection with the foregoing feature, another feature of the invention is the provision of a method of the type set forth, which involves determining the ability of the agent to selectively regulate a rate-limiting step in the bio-control of the bioavailable amount of an endogenous neuroactive steroid.

A still further feature of the invention is the provision of a method of the type set forth, wherein the rate-limiting step is a step in biosynthesis of the endogenous neuroactive steroid and/or biodegradation thereof.

Certain ones of these and other features of the invention may be attained by providing a method of screening for non-steroidal neuropsychiatric agents comprising: determining the ability of a candidate non-steroidal agent to selectively regulate or alter the central nervous system content and/or bioavailability of an endogenous neuroactive steroid.

Still further features of the invention are attained by providing a method of the type set forth which includes administering a candidate agent to a warm-blooded mammal and observing the effects of the agent in altering the bioavailability of an endogenous neuroactive steroid in the mammal.

Still other features of the invention are attained by providing a method of the type set forth, which involves administering a candidate agent to a primary culture of rodent cerebellar neurons and/or astrocytes or a cell line culture or brain slices and observing the effect in altering the amount of endogenous neuroactive steroids in the culture or brain slices.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

BRIEF DESCRIPTION OF THE DRAWING

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENT

Figures 1, 2:
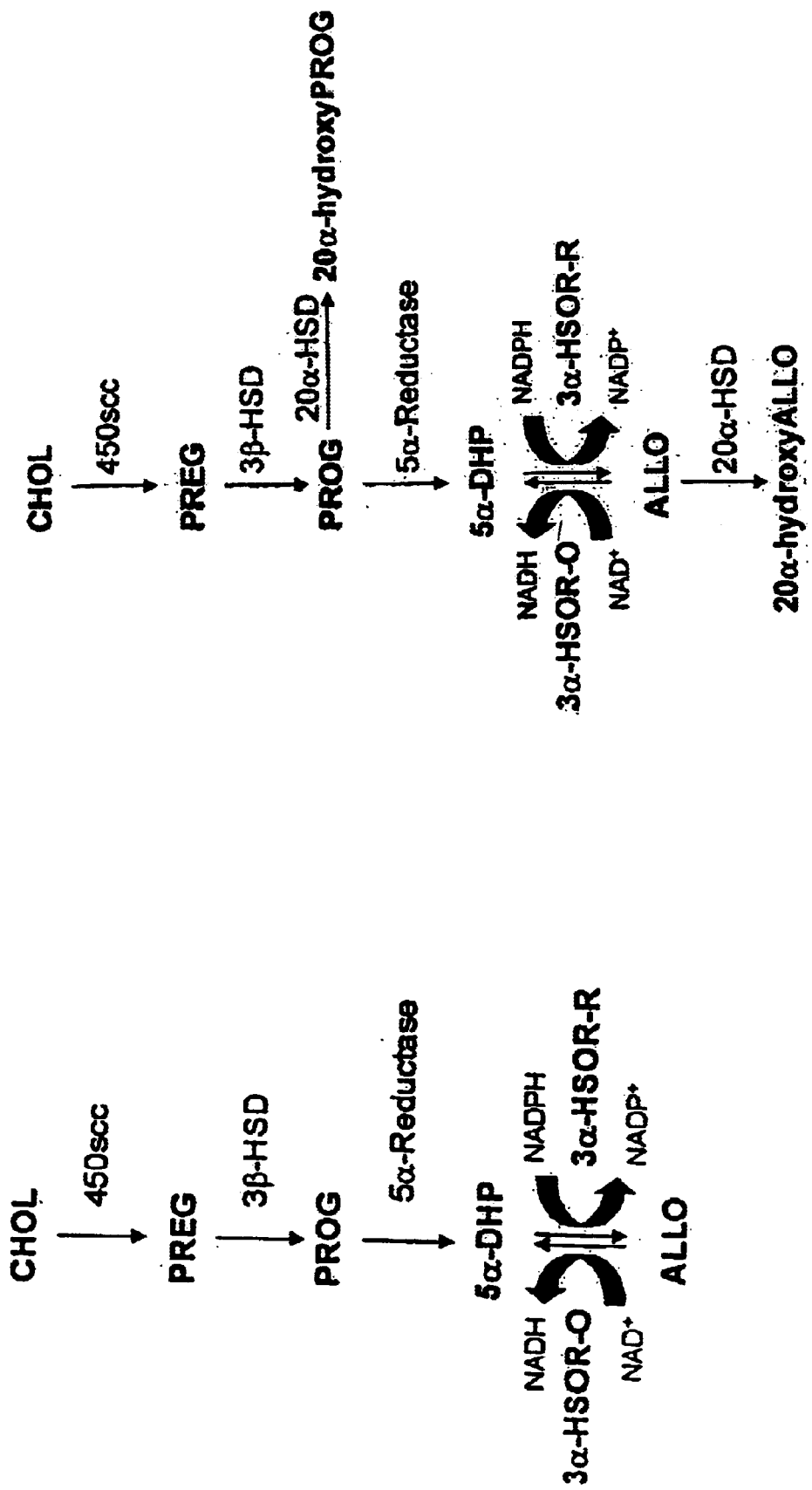
FIG. 1 is a chart of the major metabolic pathway for biosynthesis and deactivation in the CNS of a neurosteroid.
FIG. 2 is a chart similar to FIG. 1 of a metabolic pathway for deactivation of a neurosteroid in the CNS.

In recent studies we have found that fluoxetine (Prozac), a drug extensively prescribed for the treatment of major depression, affective disorders and premenstrual syndrome (PMS) administered (5–20 mg/kg, i.p.) to normal and ADX/CX male rats produced a 2–3-fold increase of brain ALLO content. Two lines of evidence point to a brain specific effect of fluoxetine, independent of a peripheral hormonal input: first, the extent of fluoxetine-induced ALLO increase was identical in normal (3 to 9 pmol/g tissue) and ADX/CX rats (2 to 8 pmol/g); second, the effect of fluoxetine was brain region specific, with a most pronounced ALLO increase occurring in the olfactory bulb, cortex, and hippocampus. Moreover, fluoxetine could increase ALLO content in vitro in rat brain slices. In additional studies we revealed that the effect of fluoxetine on brain ALLO content was dose- and time-dependent and was maintained for several hours also after protracted fluoxetine treatment.

The mechanism whereby fluoxetine increases ALLO content in the brain might be at the level of the 3α-HSOR enzyme, involving a potentiation of the reduction of 5α-DHP to ALLO or an inhibition of the oxidation of ALLO back to 5α-DHP (or both), leading to an accumulation of ALLO in the brain (see FIG. 1). Since ALLO facilitates GABA action on various $GABA_A$ receptor subtypes, the present data supports our hypothesis that this action on $GABA_A$ receptors may contribute to the antidepressant and antidysphoric actions of fluoxetine.

Furthermore, we have recently learned that the concentration of ALLO was significantly increased in the cerebrospinal fluid (CSF) of patients with unipolar major depression following 8–10 weeks of treatment with the SSRIs fluoxetine or fluvoxamine. The concentration of ALLO in the CSF of depressed patients was 16±3.1 fmol/mL and, following a successful SSRI treatment, was normalized to the levels found in the CSF of healthy controls (31±4.1 fmol/mL). The CSF content of other neurosteroids (precursors of ALLO) remained unaffected following SSRI treatment. Very interestingly, a statistically significant positive correlation existed between symptomatology improvement as measured by Hamilton Depression/Rating Scale (HAMD) scores and the extent of increase of CSF ALLO content after fluoxetine or fluvoxamine treatment. Moreover, a significant negative correlation existed between the severity of depression and ALLO levels in CSF at baseline. Collectively, this data is strongly supportive of the involvement of a mechanism of ALLO deficiency in the etiology of depression.

In further support of the invention is our recent finding that mice subjected to social-isolation stress (an established model for depression) have significantly lower brain levels of ALLO along with decreased barbiturate-induced sleeping time compared to group-housed mice. A single injection of fluoxetine (2.6 μmol/Kg i.p.), however, normalized the brain content of ALLO and barbiturate-sleeping time when administered to socially isolated mice without altering the same parameters in group-housed mice.

Recently, we also discovered that members of a new class of potent and selective ligands of the mitochondrial diazepam binding inhibitor receptor complex (MDR), the 2-aryl-3-indoleacetamide (FGIN-1) compounds, were able to potently inhibit the conversion of [$^3$H]-ALLO to [$^3$H]-5α-DHP in primary cultures of rat cerebellar neurons and astrocytes, and in a C6-2B glioma cell line. Presumably, this effect was mediated via an inhibition of the oxidative function of the 3α-HSOR by the FGIN-1 drugs. Such an effect would lead to the accumulation of ALLO, since the reverse step—the reduction of 5α-DHP to ALLO was not affected by these compounds. Similar results were obtained in brain slices of ADX/CX rats. Pretreatment of the slices with certain FGIN-1 compounds inhibited the conversion of ALLO to 5α-DHP, measured by GC/MS-NICI. Moreover, the same FGIN-1 compounds increased the rate of accumulation of ALLO following incubation of the brain slices with 5α-DHP, in a manner similar to that of fluoxetine.

Based on the experimental data, we propose that an intervention with drugs that modulate the biosynthesis and/or biodepletion of neuroactive steroids, such as 5α-DHP or ALLO, in specific brain regions, as fluoxetine does, may be beneficial for the treatment of neuropsychiatric disorders, such as depression, anxiety, panic, premenstrual dysphoria, epilepsy and others. Accordingly, we propose screening for drugs which may be beneficial in the treatment of neuropsychiatric disorders by determining their ability to modulate the biosynthesis of neuroactive steroids. Based upon the experimental data, determining such ability may be effected by administering candidate agents to rodents, such as ADX/CX rats or mice or to cultures of rat cerebellar neurons and astrocytes or cell line cultures, or brain slices, although the principles of the invention are not limited to these techniques and could utilize any techniques which would evidence the ability of the candidate agent to modulate biosynthesis of selected neuroactive steroids. Furthermore, while experimental work has identified certain neuroactive steroids, such as ALLO, the principles of the present invention would be applicable to other endogenous neuroactive steroids. Also, while the experimental evidence referred to herein relates principally to the screening of agents which may be useful in the treatment of specific neuropsychiatric disorders, it will be appreciated that the principles of the invention have general applicability to screening for agents which may be useful in any type of neuropsychiatric disorder, such as mood disorders, panic disorder, anxiety, including generalized anxiety disorder, social phobia, schizophrenia, substance abuse or addiction, post traumatic stress disorder, premenstrual dysphoric disorder, including premenstrual syndrome, and obsessive-compulsive disorder. The principles of the invention could also be used in screening for agents which may be useful in neurological disorders including epilepsy, migraine, insomnia and other sleep disorders, Alzheimer's disease, neurogenerative disorders and the like. The principles of the invention may also have applicability to screening for agents which may be useful as pre-anaesthetic medication and anti-stress medication.

From the foregoing, it can be seen that there has been provided an improved approach for utilizing the therapeutic potential of neuroactive steroids, which does not involve exogenous administration of such steroids or synthetic analogs thereof, but rather involves screening for or identifying agents which can modulate the body's own mechanisms for controlling the bioavailability of such endogenous neuroactive steroids.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawing is offered by way of illustration only and not as a limitation. The actual scope of the invention is intended to be defined in the following claims when viewed in their proper perspective based on the prior art.

We claim:

1. A method of screening for non-steroidal neuropsychiatric agents comprising:
providing a plurality of candidate non-steroidal agents not known to be neuropsychiatric agents:
for each candidate non-steroidal agent, determining the ability of the candidate non-steroidal agent to selectively increase the central nervous system content and/or bioavailability of endogenous allopregnanolone, wherein the determination comprises administering the candidate non-steroidal agent to a subject and measuring the effect of the agent on the central nervous system content and/or bioavailability of allopregnanolone in the subject, wherein an increase in the central nervous system content and/or bioavailability of endogenous allopregnanolone is predictive that the agent is a neuropsychiatric agent.

2. The method of claim 1, wherein the determining includes determining the ability of the agent to selectively regulate a rate-limiting step in the bio-control of the bioavailable amount of endogenous allopregnanolone.

3. The method of claim 2, wherein the rate-limiting step is a step in the biodegradation of endogenous allopregnanolone.

4. The method of claim 3, wherein the rate-limiting step includes inhibition of the oxidative function of the 3α-hydroxysteroid oxidoreductase that converts allopregnanolone to 5α-dihydroprogesterone.

5. The method of claim 2, wherein the rate limiting step includes steps in both the biosynthesis and the biodegradation of endogenous allopregnanolone.

6. The method of claim 1, wherein the determining includes determining the ability of the agent to affect degradation of allopregnanolone to 5α-dihydroprogesterone.

7. A method of screening for non-steroidal neuropsychiatric agents comprising:

providing a plurality of candidate non-steroidal agents not known to be neuropsychiatric agents:

for each candidate non-steroidal agent, determining the ability of the candidate non-steroidal agent to inhibit the oxidative function of the 3α-hydroxysteroid oxidoreductase that converts allopregnanolone to 5α-dihydroprogesterone, wherein an increase in the central nervous system content and/or bioavailability of endogenous allopregnanolone is predictive that the agent is a neuropsychiatric agent.

* * * * *